United States Patent [19]

Lin et al.

[11] 4,409,405

[45] Oct. 11, 1983

[54] PRODUCTION OF ETHANOL FROM METHANOL AND SYNTHESIS GAS

[75] Inventors: Jiang-Jen Lin, Round Rock; John F. Knifton, Austin, both of Tex.

[73] Assignee: Texaco Inc., White Plains, N.Y.

[21] Appl. No.: 377,724

[22] Filed: May 13, 1982

[51] Int. Cl.³ .............................................. C07C 29/00
[52] U.S. Cl. .................................................... 568/902
[58] Field of Search ........................................ 568/902

[56] References Cited

U.S. PATENT DOCUMENTS

| | | | |
|---|---|---|---|
| 4,205,190 | 5/1980 | Gane et al. | 568/902 |
| 4,262,154 | 4/1981 | Gane et al. | 568/902 |
| 4,319,056 | 3/1982 | Gane et al. | 568/902 |
| 4,357,480 | 11/1982 | Barlow et al. | 568/902 |

*Primary Examiner*—J. E. Evans
*Attorney, Agent, or Firm*—Jack H. Park; Carl G. Ries; Walter D. Hunter

[57] ABSTRACT

Ethanol is formed by contacting a mixture of carbon monoxide, hydrogen and methanol with a catalyst comprising a cobalt-containing compound and a germanium-containing compound, such as dicobalt octacarbonyl and triphenylgermanium hydride in the presence of an inert, oxygenated hydrocarbon solvent at a temperature of about 50° to about 350° C. and at a pressure of about 500 psig or greater.

18 Claims, No Drawings

PRODUCTION OF ETHANOL FROM METHANOL AND SYNTHESIS GAS

BACKGROUND OF THE INVENTION

1. Field of Invention

This invention relates to a process for the preparation of ethanol by the reaction of synthesis gas, i.e. a mixture of hydrogen and carbon monoxide, with methanol in the presence of an inert, oxygenated solvent using as a catalyst a combination of a cobalt-containing compound and a germanium-containing compound.

2. Prior Art

There is an increasing commercial potential for use of ethanol as a gasoline extender. As petroleum supplies are shifting, the synthesis gas technology area is gaining importance.

A great number of processes have been described in the art for reacting methanol with carbon monoxide and hydrogen in the presence of catalyst systems to produce ethanol. A general disadvantage of the art described processes is that they all produce a wide variety of other related products such as higher molecular weight alcohols, aldehydes, hydrocarbons, carboxylic acids, esters, etc. in addition to the desired ethanol.

In U.S. Pat. No. 3,285,948, for example, a method of forming alcohols is set out in which a cobalt catalyst system comprising cobalt carbonyl, a promoter and a ruthenium halide is described. Methanol homologation to ethanol has also been disclosed in U.S. Pat. Nos. 4,133,966, 4,239,924 and 4,239,925 wherein the three component catalyst systems consist of a cobalt-containing compound, a first promoter comprising an iodine compound and a second promoter comprising a ruthenium compound. Taylor, in U.S. Pat. No. 4,111,837, describes an improved process for converting methanol into ethanol and ethanol precursors using a cobalt carbonyl catalyst coupled with a novel heterogeneous cocatalyst system such as rhenium metal. Walker, in U.S. Pat. No. 4,277,634 and Riley et.al. in U.S. Pat. No. 3,248,432, teach the preparation of ethanol by the reaction of methanol, carbon monoxide, and hydrogen in the presence of a cobalt compound and an iodine promoter. Likewise in British Pat. No. 1,546,428 the preparation of ethanol is by reacting methanol with carbon monoxide and hydrogen in the presence of a solvent such as hydrocarbon solvent, a cobalt-containing catalyst such as cobalt iodide or bromide and a tertiary phosphine. Slinkard in U.S. Pat. No. 4,168,391 teaches a process for preparing ethanol by reaction of carbon monoxide, hydrogen and methanol in the presence of cobalt carbonyl and an oxygenated solvent such as dioxane.

All of the processes described above suffer from one or more disadvantages. In most cases the conversion of methanol is low, decomposition of the catalyst to insoluble and inactive species is observed, and a wide variety of products in addition to the desired ethanol are formed with consequent separation and disposal problems.

SUMMARY OF THE INVENTION

In the process of this invention ethanol is prepared in high yield by reacting methanol with a mixture of hydrogen and carbon monoxide. More particularly, this invention relates to a process for preparing ethanol by contacting methanol, hydrogen, and carbon monoxide with a catalyst system comprising a cobalt-containing compound and a germanium-containing compound in the presence of an oxygenated hydrocarbon solvent at an elevated temperature and pressure.

Recovery of ethanol from the reaction product can be carried out in any conventional or convenient manner such as by distillation, extraction, etc.

The high selectivity to ethanol achieved in this process ranges up to a value of 64 wt. percent while conversions of methanol reach the very high figure of 94 wt. percent. Other advantages include the production of acetaldehyde as a major by product and a stable catalyst system which may be recycled.

DETAILED DESCRIPTION OF THE INVENTION

This invention relates to a process for preparing ethanol by a process which comprises reacting a mixture of hydrogen, carbon monoxide and methanol in the presence of a catalyst system comprising a cobalt-containing compound and a germanium-containing compound at superatmospheric pressures of about 500 psi or greater and at a temperature of about 50° to about 350° C. and in the presence of an inert, oxygenated hydrocarbon solvent.

Generally, with regard to the metallic components of the catalyst system, the system will contain from about 20 to about 85 mole percent of cobalt compound with the balance being the germanium-containing compound, based on the total number of moles of cobalt compound and total number of moles of germanium compound in the system. Preferably, the catalyst system will contain about equimolar amounts of cobalt and germanium compounds.

Catalysts that are suitable for use in the practice of this invention contain a cobalt compound as well as a germanium compound. The cobalt-containing compounds and the germanium-containing compounds may be chosen from a wide variety of organic or inorganic compounds, complexes, etc., as will be shown and illustrated below. It is only necessary that the catalyst precursor actually employed contain said metals in any of their ionic states. The actual catalytically active species is then believed to comprise cobalt and germanium in complex combination with one or more ligands and with carbon monoxide and hydrogen. The most effective catalyst is achieved where the cobalt and the germanium species are solubilized in the methanol coreactant and the oxygenated hydrocarbon.

As previously pointed out in the process of this invention the reaction is conducted in the presence of a catalyst which includes a cobalt-containing compound. The cobalt-containing compound employed may be a cobalt carbonyl or a compound capable of forming a cobalt carbonyl under reaction conditions.

The cobalt-containing catalyst precursors may take many different forms. For instance, the cobalt may be added to the reaction mixture in an oxide form, as in the case of, for example, cobalt(II) oxide (CoO) or cobalt-(II, III) oxide ($Co_3O_4$). Alternatively, it may be added as the salt of a mineral acid, as in the case of cobalt(II) chloride ($CoCl_2$), cobalt(II) chloride hydrate ($CoCl_2.6H_2O$), cobalt(II) bromide ($CoBr_2$), cobalt(II) iodide ($CoI_2$) and cobalt (II) nitrate hydrate ($Co(NO_3)_2.6H_2O$), etc., or as the salt of a suitable organic carboxylic acid, for example, cobalt(II) formate, cobalt(II) acetate, cobalt(II) propionate, cobalt naphthenate, cobalt acetylacetonate, etc. The cobalt may be added to the reaction zone as a carbonyl or hydrocarbonyl derivative. Here, suitable examples include dicobalt octacarbonyl ($Co_2(CO)_8$), cobalt hydrocarbonyl ($HCo(CO)_4$) and substituted carbonyl species such as the triphenylphosphine cobalt tricarbonyl dimer, etc.

Preferred cobalt-containing compounds include oxides of cobalt, cobalt salts of a mineral acid, cobalt salts of organic carboxylic acids and cobalt carbonyl or hydrocarbonyl derivatives. Among these, particularly preferred are cobalt(II) chloride, cobalt(III) acetylacetonate, cobalt(II) acetate, cobalt(II) propionate, and especially preferred are dicobalt octacarbonyl and cobalt iodide.

The germanium-containing compounds which may be utilized with the cobalt-containing compounds in this process may also take many different forms. For instance, the germanium may be added to the reaction mixture in the form of a halide, such as germanium tetrachloride, germanium diiodide and germanium tetrabromide, or as a hydrocarbylgermanium compound such as tetra-n-butylgermane, tetraethylgermane, tetraphenylgermane and tetramethylgermane, or as an organo-halide germanium compound such as diphenylgermanium chloride, methylgermanium trichloride, phenylgermanium trichloride, tri-n-butylgermanium iodide, trimethylgermanium chloride, triphenylgermanium bromide and triphenylgermanium chloride or an organo-germanium hydride such as triphenylgermanium hydride, or an organogermanium oxide or carboxylate such as triphenylgermanium acetate, or a germanium alkoxide such as germanium butoxide, germanium ethoxide and germanium methoxide.

The preferred germanium-containing promoter compounds are the organo-halide germanium compounds, the hydrocarbylgermanium compounds and the organogermanium hydrides. Among these, particularly preferred are triphenylgermanium bromide, trimethylgermanium chloride, triphenylgermanium chloride, triethylgermanium chloride, tetramethylgermane, and especially preferred are tetraphenylgermane and triphenylgermanium hydride.

The number of gram moles of the germanium-containing compound per gram atom of cobalt can be varied widely in this process and is generally in the range of 0.01 to 100 and preferably from 0.1 to 5.0.

The quantity of cobalt catalyst employed in the instant invention is not critical and may vary over a wide range. In general, the novel process is desirably conducted in the presence of a catalytically effective quantity of one or more of the active cobalt species together with one or more of the germanium-containing promoters which gives the desired products in reasonable yields. The reaction proceeds when employing as little as about $1 \times 10^{-6}$ weight percent and even lesser amounts of cobalt, basis the total weight of the reaction mixture. The upper concentration is dictated by a variety of factors including catalyst cost, partial pressures of carbon monoxide and hydrogen, operating temperature, etc. A cobalt catalyst concentration of from about $1 \times 10^{-5}$ to about 10 weight percent cobalt, based on the total weight of reaction mixture, is generally desirable in the practice of this invention.

The solvents useful in the process of this invention are oxygenated hydrocarbons, e.g., compounds composed of carbon, hydrogen and oxygen in which the only oxygen atoms present are in ether group, ester groups, ketone groups or hydroxyl groups of alcohols. Generally, the oxygenated hydrocarbon will contain 3 to 12 carbon atoms. The solvent must be substantially inert under reaction conditions and it must be one which has a normal boiling point of at least 40° C. at atmospheric pressure and preferably, the solvent will have a boiling point greater than that of ethanol and other oxygen-containing reaction products so that recovery of the solvent by distillation is facilitated.

Preferred ester-type solvents are the aliphatic and acylic carboxylic acid monoesters as exemplified by butyl acetate, methyl benzoate, isopropyl iso-butyrate and propyl proprionate as well as dimethyl adipate. Useful alcohol-type solvents include monohydric alcohols such as cyclohexanol, 1-hexanol, neopentanol, 2-octanol, etc. Suitable ketone-type solvents include, for example, cyclic ketones, such as cyclohexanone and 2-methylcyclohexanone, as well as acyclic ketones such as 2-pentanone, butanone, acetophenone, etc. Ethers which may be utilized as solvents include cyclic, acyclic and heterocyclic materials. Preferred ethers are the heterocyclic ethers as illustrated by 1,4-dioxane and 1,3-dioxane. Other suitable ether solvents include di-n-propyl ether, diethylene glycol dibutyl ether, dibutyl ether, ethyl butyl ether, diphenyl ether, heptyl phenyl ether, anisole, tetrahydrofuran, etc. The most useful solvents of all of the above group include the ethers as represented by monocyclic, heterocyclic ethers such as p-dioxane, etc.

The relative amounts of carbon monoxide and hydrogen which may be initially present in the syngas mixture are also variable, and these amounts may be varied over a wide range. In general, the mole ratio of $CO:H_2$ is in the range from 20:1 up to about 1:20, preferably from about 5:1 to 1:5, although ratios outside these ranges may also be employed. Particularly in continuous operations, but also in batch experiments, the carbon monoxide-hydrogen gaseous mixtures may also be used in conjunction with up to 50% by volume of one or more inert gases such as nitrogen, argon, neon and the like, or they may include gases that may, or may not, undergo reaction under CO hydrogenation conditions such as carbon dioxide, hydrocarbons such as methane, ethane, propane and the like, ethers such as dimethyl ether, methylethyl ether and diethyl ether.

The temperature range which can usefully be employed in these synthesis is a further variable, dependent upon other experimental factors, including the pressure, and the concentration and choice of particular species of the cobalt-containing compound and germanium compounds, among other things. The range of operability is from about 50° to about 350° C. when superatmospheric pressures of syngas are employed. A narrower range of about 100° to about 250° C. represents the preferred temperature range.

Superatmospheric pressure of about 500 psi or greater leads to substantial yields of desirable ethanol by the process of this invention. A preferred operating range is from about 1000 psi to about 10,000 psi although pressures above 10,000 psi also provide useful yields of the desired products. The pressures referred to here represent the total pressure generated by all the reactants, although they are substantially due to the carbon monoxide and hydrogen fractions in these examples.

As far as can be determined, without limiting the invention thereby, the one-step process herein utilizing the disclosed catalysts leads primarily to the formation of ethanol and acetaldehyde. By-products such as water, n-propanol, methylacetate, ethyl acetate and acetic acid are also detected in the liquid products fraction.

The novel process of this invention can be conducted in a batch, semicontinuous or continuous fashion. The catalyst may be initially introduced into the reaction zone batchwise, or it may be continuously or intermittently introduced into such a zone during the course of the synthesis reaction. Operating conditions can be adjusted to optimize the formation of the desired alcohol products, and said material may be recovered by methods well known in the art, such as distillation, fractionation, extraction and the like. A fraction rich in the cobalt-containing compound and the promoter compound may then be recycled to the reaction zone, if desired, and additional products generated.

The products formed by the process of this invention have been identified in this work by one or more of the following analytical procedures, viz, gas-liquid phase chromatograph (glc), infrared (ir), mass spectrometry, nuclear magnetic resonance (nmr) and elemental analysis, or a combination of these techniques. Analysis have, for the most part, been by parts per weight; all temperatures are in degrees centrigrade and all pressures in pounds per square inch gauge (psig).

To illustrate the process of the invention, the following examples are given. It is understood, however, that the examples are given in the way of illustration and are not to be regarded as limiting the invention in any way.

EXAMPLE I

A glass lined pressure reactor was charged with a mixture of 0.34 g (1 mmole) of dicobalt octacarbonyl, 0.304 g (1 mmole) triphenylgermanium hydride, 5.6 g methanol and 14.0 g p-dioxane. The reactor was purged of air and pressured to 1000 psig with a mixture of carbon monoxide and hydrogen (1:2 molar ratio), then was heated to 180° C. while it was agitated by rocking. The pressure was brought up to 4000 psig by the addition of an amount of the carbon monoxide-hydrogen mixture. The reaction was continued for 18 hours and at the end of this time the pressure was 3000 psig. The reaction was stopped and the reactor allowed to cool to room temperature. An off-gas sample was taken, and excess gas vented from the reactor, following which 26.1 g of dark brown liquid product was recovered.

The product liquid was analyzed by GLC. The carbon selectivities to ethanol, acetaldehyde, n-propanol, methyl acetate and ethyl acetate products (basis methanol converted) were then estimated to be as follows:

56 wt. % ethanol
7 wt. % acetaldehyde
7 wt. % n-propanol
4 wt. % methyl acetate
2 wt. % ethyl acetate The methanol conversion was calculated to be 61%. The water content of the crude liquid product was determined by Karl Fischer titration to be 7.67 wt. %. A typical off-gas sample showed the presence of:

53.9% hydrogen
41.1% carbon monoxide
1.7% methane
0.58% carbon monoxide

EXAMPLE II

To a glass lined pressure reactor was charged a mixture of 0.34 g (1 mmole) of dicobalt octacarbonyl, 0.080 g (0.25 mmole) triphenylgermanium hydride, 5.6 g methanol and 14.0 g p-dioxane. The reactor was purged of air and pressured to 1000 psi with a mixture of carbon monoxide and hydrogen (1:2 molar ratio), then was heated to 175° C. while it was agitated by rocking. The pressure was brought up to 4200 psig through the addition of an amount of the carbon monoxide-hydrogen mixture from a surge tank. The reaction was continued for 18 hours and at the end of the reaction period the pressure was 3800 psig. The reaction was stopped and the reactor allowed to cool to room temperature. An off-gas sample was taken and excess gas vented from the reactor following which 24.1 g of a dark brown liquid product was recovered.

Samples of the liquid product were analyzed by GLC, the product selectivities were estimated to be:

54 wt. % ethanol
8 wt. % acetaldehyde
5 wt. % methyl acetate
3 wt. % ethyl acetate The methanol conversion was calculated to be 79%. The water content as determined by Karl Fischer titration was 11.1 wt. %.

EXAMPLE III

The pressure reactor was charged with a mixture of 0.34 g (1.0 mmoles) of dicobalt octacarbonyl, 0.38 g (1.0 mmoles) tetraphenylgermane, 5.6 g methanol and 14.0 g p-dioxane. The reactor was purged of air and pressured to 1000 psig with a mixture of carbon monoxide and hydrogen (1:2 molar ratio), then was heated to 180° C. while it was agitated by rocking. The pressure was brought up to 4175 psig from a surge tank containing the 1:2 molar carbon monoxide-hydrogen mixture. The reaction was continued for 18 hours and at the end of the reaction period the pressure was 3975 psig. The reaction was stopped and the reactor was allowed to cool to room temperature. An off-gas was taken and excess gas vented from the reactor following which 21.4 g of dark brown liquid product was recovered.

Samples of the liquid product were analyzed by GLC and the product selectivities were estimated as follows:

53.0 wt. % ethanol
7.0 wt. % acetaldehyde
3.0 wt. % methyl acetate

The methanol conversion was calculated to be 63 wt. %. The water content was determined by Karl Fischer titration as 5.18%.

EXAMPLE IV

A glass lined pressure reactor was charged with a mixture of 0.34 g (1.0 mmoles) of dicobalt octacarbonyl, 0.384 g (1.0 mmoles) triphenylgermanium bromide, 5.6 g methanol and 14.0 g p-dioxane. The reactor was purged of air and pressured to 1000 psig with a mixture of carbon monoxide and hydrogen (1:2 molar ratio), then was heated to 180° C. while it was agitated by rocking. The pressure was brought up to 4220 psig from a surge tank containing the 1:2 molar carbon monoxide-hydrogen mixture and was maintained at that pressure the 4 hours of the procedure. The reaction was stopped and the reactor was allowed to cool to room temperature. An off-gas was taken and excess gas vented from the reactor following which 22.2 g of dark brown liquid product was recovered.

Samples of the liquid product were analyzed by GLC and the product selectivities were estimated to be:

34.0 wt. % ethanol
14.0 wt. % acetaldehyde
18.0 wt. % ethyl acetate

The methanol conversion was calculated to be 36 wt. %. The water content was determined by Karl Fischer titration as 5.81 wt. %.

EXAMPLE V

Following the general procedure of Examples I to IV inclusive, a glass lined reactor was charged with 0.34 g (1 mmole) of dicobalt octacarbonyl, 0.30 g (1 mmole) triphenylgermanium hydride, 5.6 g methanol and 14.0 g of p-dioxane. The reactor was purged of air and pressured to 1000 psig with a mixture of carbon monoxide and hydrogen (1:2 molar ratio), then was heated to 175° C. while it was agitated by rocking. The pressure was brought up to 4000 psig through addition of the carbon monoxide-hydrogen mixture from a surge tank. The reaction was continued for 18 hours. The reaction was stopped and the reactor was allowed to cool to room temperature, an off-gas was taken and excess gas vented from the reactor, following which 22.5 g of dark brown liquid product was recovered.

Analysis of the liquid product by GLC gave the following product selectivities:

44.0 wt. % ethanol
4.0 wt. % n-propanol
10.0 wt. % acetaldehyde
4.0 wt. % ethyl acetate
8.0 wt. % acetic acid The methanol conversion was calculated to be 60 wt. %. The water content of the same crude liquid product was determined by Karl Fischer titration to be 8.54 wt. %. The cobalt content of this same liquid product was shown, by atomic absorption, to be 4605 ppm, this represents a 90% cobalt recovery in solution.

The remaining liquid product from the experiment, after completion of the analytical testing, was subject to fractional distillation at atmospheric pressure and the distillate fractions were collected. The residual catalyst liquid (3.5 g) was then combined with fresh methanol (5.6 g) and p-dioxane (14.0 g) and charged to the glass-lined reactor. The reactor was sealed, purged of air, pressured to 1000 psi with carbon monoxide and hydrogen (1:2 molar ratio) and heated to 175° C. with agitation. The pressure was brought up to 4000 psig and the reaction continued for 18 hours. The liquid product recovered as in the first cycle analysis of this product by GLC gave the following selectivities:

50 wt. % ethanol
6.0 wt. % n-propanol
10.0 wt. % acetaldehyde
5.0 wt. % ethyl acetate
9.0 wt. % acetic acid Methanol conversion was 60 wt. %.

The crude liquid product from this second catalyst cycle was then subject to the same fractional distillation described SUPRA, and the residual catalyst solution (2.0 g) returned to the reactor along with fresh methanol (5.6 g) and p-dioxane (14.0 g), for a third cycling of the cobalt-germanium catalyst, under the same reaction conditions. The liquid product, recovered as in the first and second cycles, was analyzed by GLC with the following results:

48.0 wt. % ethanol
5.0 wt. % n-propanol
11.0 wt. % acetaldehyde
4.0 wt. % ethylacetate Methanol conversion was 60 wt. %.

Data for this three cycle experiment, using the same sample of dicobalt octacarbonyl-triphenylgermanium hydride catalyst, are summarized in Table I. The methanol conversion and ethanol selectivity for this 3-cycle experiment are shown in Table 1.

TABLE 1

Synthesis of Ethanol from Methanol and Syngas
Catalyst Recycling

| Number of Catalyst Cycles | Methanol Conversion % | Ethanol Selectivity Wt. % |
|---|---|---|
| 1 | 60 | 44 |
| 2 | 60 | 50 |
| 3 | 60 | 48 |

It is evident from this data that the dicobalt octacarbonyl-triphenylgermanium hydride catalyst system remains active for methanol homologation to ethanol even after recycling of the same catalyst sample.

EXAMPLE VI

In this comparative example the experimental procedure of Example I is followed except no germanium-containing compound was added to the reaction charge.

A mixture of dicobalt octacarbonyl (0.34 g, 1.0 mmole), methanol (5.6 g) and p-dioxane (14.0 g) were introduced into the glass-lined reactor. The reactor was purged of air and pressured to 1000 psi with a mixture of carbon monoxide and hydrogen (1:2 molar ratio), then was heated to 180° C. while it was agitated by rocking. The pressure was brought up to 3975 psi with the mixture of carbon monoxide and hydrogen. The reaction was continued for 18 hours and at the end of the reaction period the pressure was 2200 psi. The reaction was stopped and the reactor allowed to cool to room temperature. An off-gas sample was taken and excess gas vented from the reactor following which 22.2 g of green solution was recovered.

Analysis of the liquid product by GLC showed the following product selectivities:

64 wt. % ethanol
9 wt. % n-propanol
4 wt. % acetaldehyde
3 wt. % methyl formate

Methanol conversion was estimated to be 78 wt. %.

The cobalt content of the crude liquid product, as determined by atomic absorption, was found to be 122 ppm. This figure represents a 3% recovery of cobalt in solution, basis the quantity of dicobalt octacarbonyl originally charged.

EXAMPLE VII

In another embodiment of the process of this invention, a glass lined pressure reactor was charged with a mixture of 0.68 g (2 mmoles) of cobalt(II) iodide, 0.74 g (2 mmoles) tetraphenylgermane, 5.6 g methanol and 14.0 g p-dioxane. The reactor was purged of air and pressured to 1000 psig with a mixture of carbon monoxide and hydrogen (1:2 molar ratio), then was heated to 180° C. while it was agitated by rocking. The pressure was brought up to 2000 psig from a surge tank containing the 1:2 molar carbon monoxide-hydrogen mixture. The reaction was continued for 18 hours, the reactor cooled and vented and 24.5 g of dark brown liquid product was recovered.

Analysis of the liquid product by GLC showed the following product selectivities:

59 wt. % ethanol
15 wt. % acetaldehyde
3 wt. % n-propanol
4 wt. % methyl acetate
3 wt. % ethyl acetate The methanol conversion was calculated to be 94%. The water content was determined by Karl Fischer titration to be 13.6%. The cobalt content of the crude liquid product was determined to be 4985 ppm. This figure represents a >99% recovery in solution of the cobalt originally charged as cobalt iodide.

EXAMPLE VIII

Following the procedures of Example I, the glass-lined pressure reactor was charged with a mixture of 0.68 g (2 mmole) of cobalt(II) iodide, 0.304 g (1 mmole) triphenylgermanium hydride, 5.6 g methanol and 14.0 g of p-dioxane. The reactor was purged of air and pressured to 1000 psig with a mixture of carbon monoxide and hydrogen (1:2 molar ratio), then was heated to 180° C. while it was agitated by rocking. The pressure was brought up 2000 psig through the addition of $CO/H_2$ (1:2) from a surge tank. The reaction was continued for 18 hours, the reactor cooled and vented, and the dark-brown liquid product was recovered. and Analysis of the liquid product by GLC showed the following product selectivities:

60 wt. % ethanol
15 wt. % acetaldehyde
2 wt. % n-propanol
3 wt. % methyl acetate
2 wt. % ethyl acetate The methanol conversion was calculated to be 88%. The water content was determined by Karl Fischer titration as 13.2%.

EXAMPLE IX

A glass lined pressure reactor was charged with a mixture of 0.34 g (1 mmole) of cobalt iodide, 0.38 g (1 mmole) triphenylgermanium hydride, 5.6 g methanol and 14.0 g p-dioxane. The reactor was purged of air and pressured to 1000 psig with a mixture of carbon monoxide and hydrogen (1:2 molar ratio), then was heated to 180° C. while it was agitated by rocking. The pressure was brought up to 4250 psig from a surge tank containing the 1:2 molar carbon monoxide-hydrogen mixture. The reaction was continued for 18 hours and at the end of the reaction period the pressure was 4000 psig. The reaction was stopped and the reactor was allowed to cool to room temperature. An off-gas was taken and excess gas vented from the reactor following which 20.0 g of dark brown product was recovered.

Analysis of the liquid product by GLC showed the following product selectivities:

58 wt. % ethanol
14.0 wt. % acetaldehyde
8.0 wt. % n-propanol
3.0 wt. % methyl acetate
3.0 wt. % ethyl acetate The methanol conversion was calculated to be 93.0%. The water content was determined by Karl Fischer titration as 15.1%.

EXAMPLE X

In the comparative example, the experimental procedure of Example VII was followed, but no germanium compound was present in this run.

A mixture of cobalt(II) iodide (0.68 g, 2.0 mmole), methanol (5.6 g), and p-dioxane (14.0 g) is charged to the glass-lined reactor. The reactor was purged of air and pressured to 1000 psi with a mixture of carbon monoxide and hydrogen (1:2 molar ratio). Then was heated to ca 180° C. while is was agitated by rocking. The pressure was brought up to 2000 psi and maintained by a surge tank. The reaction was continued for 18 hours and allowed to cool to room temperature. (1500 psi pressure noted). The excess gas vented from the reactor and a brown solution with some purple precipitate was recovered (23.4 g).

Analysis of the liquid product by GLC showed the following product selectivities:

29 wt. % ethanol
3 wt. % n-propanol
29 wt. % acetaldehyde
0 wt. % methyl acetate
8 wt. % ethyl acetate The methanol covering was calculated to be 92%.

The cobalt content of the crude liquid product was determined to be 3717 ppm, this figure represents a 74% recovery in solution of the cobalt originally charged as cobalt iodide.

It may be noted in this example-using the cobalt iodide catalyst with no germanium component-provided considerably lower ethanol selectivity (29%) and lower cobalt recovery (74%) than in Example VII-with the cobalt iodide-tetraphenylgermane catalyst.

What is claimed is:

1. A process for preparing ethanol which comprises contacting a mixture of carbon monoxide, hydrogen and methanol with a catalyst system comprising a cobalt-containing compound and a germanium-containing compound in the presence of an inert oxygenated hydrocarbon solvent and at a pressure of 500 psi or greater and at a temperature of about 50° to about 350° C.

2. The process of claim 1 wherein the process is conducted at a pressure of about 2000 psig to about 10,000 psig.

3. The process of claim 1 wherein the process is conducted at a temperature of about 100° to about 250° C.

4. The process of claim 1 wherein the said cobalt-containing compound is selected from the group consisting of one or more oxides of cobalt, cobalt salts of a mineral acid, cobalt salts of an organic carboxylic acid and cobalt carbonyl or hydrocarbonyl derivatives.

5. The process of claim 1 wherein the said cobalt-containing compound is selected from the group consisting of cobalt(II) oxide, cobalt chloride, cobalt(II) iodide, cobalt nitrate, cobalt sulfate, cobalt(II) acetate, cobalt(II) propionate, cobalt(II) acetylacetonate, and dicobalt octacarbonyl.

6. The process of claim 1 wherein said cobalt containing compound is dicobalt octacarbonyl.

7. The process of claim 1 wherein the said cobalt compound is cobalt(II) iodide.

8. The process of claim 1 wherein the said germanium-containing compound is selected from the group consisting of triphenylgermanium hydride, tetraphenylgermane, tetraethylgermane, triphenylgermanium chloride, trimethylgermanium bromide and triethylgermanium chloride.

9. The process of claim 1 wherein the said germanium-containing compound is triphenylgermanium hydride.

10. The process of claim 1 wherein the said germanium-containing compound is tetraphenylgermane.

11. The process of claim 1 wherein the said germanium-containing compound is triphenylgermanium bromide.

12. The process of claim 1 wherein said oxygenated hydrocarbon solvent is selected from the group consisting of 1,3-dioxane, 1,4-dioxane, isopropyl ether, diethylene glycol dibutyl ether, dibutyl ether and ethylbutyl ether.

13. The process of claim 1 wherein the said oxygenated hydrocarbon solvent is p-dioxane.

14. The process of claim 1 wherein the said cobalt-containing compound is cobalt iodide, the said germanium-containing compound is tetraphenylgermane, and the said solvent is p-dioxane.

15. The process of claim 1 wherein the said cobalt-containing compound is cobalt iodide, the said germanium promoter is triphenylgermanium hydride, and the said solvent is p-dioxane.

16. The process of claim 1 wherein the said cobalt-containing compound is dicobalt octacarbonyl, the said germanium-containing compound is triphenylgermanium bromide, and the said solvent is p-dioxane.

17. The process of claim 1 wherein the said cobalt-containing compound is dicobalt octacarbonyl, the said germanium compound is tetraphenylgermane and the said solvent is p-dioxane.

18. The process of claim 1 wherein the said cobalt-containing compound is dicobalt octacarbonyl, the said germanium-containing compound is triphenylgermanium hydride and the said solvent is p-dioxane.

* * * * *